United States Patent [19]

Muia et al.

[11] Patent Number: 5,457,083

[45] Date of Patent: Oct. 10, 1995

[54] SYNERGISTIC ANTIMICROBIAL COMBINATION OF POLYETHER PHOSPHONATES AND NON-OXIDIZING BIOCIDES

[75] Inventors: Ramon A. Muia; Nancy S. Sherwood, both of Coraopolis, Pa.

[73] Assignee: Calgon Corporation, Pittsburgh, Pa.

[21] Appl. No.: 961,578

[22] Filed: Oct. 15, 1992

[51] Int. Cl.$^6$ .................................................. A01N 57/04
[52] U.S. Cl. .......................... 504/128; 504/127; 504/148; 504/153; 504/158; 514/108; 514/367; 514/369; 514/515; 514/578; 514/579; 514/599; 514/626; 514/634; 514/740
[58] Field of Search ....................... 504/127, 148, 504/158, 153, 128; 514/634, 108, 367, 369, 515, 578, 579, 599, 626, 740

[56] References Cited

U.S. PATENT DOCUMENTS

| | | | |
|---|---|---|---|
| 3,065,123 | 11/1962 | Hinton et al. | 162/161 |
| 3,628,941 | 12/1971 | Marks | 514/634 |
| 3,833,731 | 9/1974 | Grier et al. | 514/526 |
| 3,873,597 | 3/1975 | Harmetz et al. | 558/454 |
| 3,877,922 | 4/1975 | Grier et al. | 504/150 |
| 3,970,755 | 7/1976 | Gazzard et al. | 514/373 |
| 4,464,276 | 8/1984 | Snug et al. | 548/265.6 |
| 4,604,405 | 8/1986 | Jakubowski | 514/526 |
| 4,612,328 | 9/1986 | Jakubowski | 514/515 |
| 4,647,589 | 3/1987 | Valone | 514/627 |
| 4,655,815 | 4/1987 | Jakubowski | 504/133 |
| 4,661,503 | 4/1987 | Martin et al. | 514/372 |
| 4,830,657 | 5/1989 | Jakubowski et al. | 504/138 |
| 4,931,189 | 6/1990 | Dhawan et al. | 210/700 |
| 5,041,463 | 8/1991 | Whitekettle et al. | 514/634 |

FOREIGN PATENT DOCUMENTS

| | | |
|---|---|---|
| 1458041 | 6/1972 | United Kingdom . |
| 1531431 | 1/1975 | United Kingdom . |

*Primary Examiner*—Allen J. Robinson
*Assistant Examiner*—Brian Bembenick
*Attorney, Agent, or Firm*—Craig G. Cochenour; William C. Mitchell

[57] ABSTRACT

Synergistic antimicrobial combinations of polyether polyamino methylene phosphonates and one or more members selected from the group consisting essentially of the following non-oxidizing biocides:
didecyl dimethyl ammonium chloride;
dodecylguanidine hydrochloride;
methylene bisthiocyanate;
2,2-dibromo-3-nitrilo-propionamide;
2-(thiocyanomethylthio)benzothiazole glutaraldehyde;
potassium dimethyldithiocarbamate;
5-chloro-2-methyl-4-isothiazolin-3-one;
2-methyl-4-isothiazolin-3-one;
tetrahydro-3,5-dimethyl-2,H-1,3,5-thiadiazin-2-thione;
1,2-dibromo-2,4-dicyanobutane;
are useful for inhibiting microbial growth in a variety of aqueous systems.

5 Claims, No Drawings

5,457,083

SYNERGISTIC ANTIMICROBIAL COMBINATION OF POLYETHER PHOSPHONATES AND NON-OXIDIZING BIOCIDES

BACKGROUND OF THE INVENTION

1. Field of the Invention

The present invention is concerned with antimicrobial compositions which are useful for inhibiting microbial growth wherever such microbial growth is undesirable, e.g., aqueous systems found in a variety of industrial applications, such as papermaking.

In particular, the present invention is concerned with antimicrobial compositions which comprise a synergistic mixture of two components. One component is a polyether polyamino methylene phosphonate, which has also been found to exhibit excellent calcium carbonate scale inhibition under the severe conditions of high calcite concentration and high pH which characterize, e.g., a cycled up cooling tower. Thus, control of unwanted microbial growth in such systems is provided in addition to scale control; however, the present invention is not limited to such applications.

The other component of the synergistic mixture is a non-oxidizing biocide, which is one or more members selected from the group consisting essentially of those detailed further herein. All of these non-oxidizing biocides, as well as combinations thereof, are well known in the antimicrobial art. However, the discovery that these conventional non-oxidizing biocides could form the basis for synergistic combinations with the polyether phosphonates described herein, was both surprising and unexpected.

As used herein, the phrases, "antimicrobial" and "inhibiting microbial growth" describe the killing of or destruction of, as well as the inhibition of or control of the growth or propagation of bacteria, fungi (including yeasts and molds) and algae in dormant, immature developing and/or mature stages. A number of important industries can experience serious adverse effects from the activity of such bacteria and fungi on the raw materials which they employ, on various aspects of their manufacturing activities, or on the finished products which they produce. Such industries include the paint, wood, textile, cosmetic, leather, tobacco, fur, rope, paper, pulp, plastics, fuel, oil, rubber, and machine industries. Important applications of the synergistic antimicrobial combination of the present invention include: inhibiting the growth of bacteria and fungi in aqueous paints, adhesives, latex emulsions, and joint cements; preserving wood; preserving cutting oils; controlling slime-producing bacteria and fungi in pulp and paper mills and cooling waters; as a spray or dip treatment for textiles and leather to prevent mold growth; as a component of anti-fouling paints to prevent adherence of fouling organisms; protecting paint films, especially exterior paints, from attack by fungi which occurs during weathering of the paint film; protecting processing equipment from slime deposits during manufacture of cane and beet sugar; preventing microorganism buildup and deposits in air washer or scrubber systems and in industrial fresh water supply systems; controlling microorganism contamination and deposits in oil field drilling fluids and muds, and in secondary petroleum recovery processes; preventing bacterial and fungal growth in paper coating processes which might adversely affect the quality of the paper coating; controlling bacterial and fungal growth and deposits during the manufacture of various specialty boards, e.g., cardboard and particle board; preventing sap stain discoloration on freshly cut wood of various kinds; controlling bacterial and fungal growth in clay and pigment slurries of various types which are manufactured for later use in paper coating and paint manufacturing for example, and which are susceptible to degradation by microorganisms during storage and transport; as a hard surface disinfectant to prevent growth of bacteria and fungi on walls, floors, etc.; and in swimming pools to prevent algae growth.

The control of bacteria and fungi in pulp and paper mill water systems which contain aqueous dispersions of papermaking fibers is especially important. The uncontrolled buildup of slime produced by the accumulation of bacteria and fungi causes offgrade production, decreased production due to breaks and greater cleanup frequency, increased raw material usage, and increased maintenance costs. The problem of slime deposits has been aggravated by the widespread use of closed white water systems in the paper industry.

Another important area where control of bacterial and fungal growth is vital is in clay and pigment slurries. These slurries are of various clays, e.g. kaolin, and pigments, e.g. calcium carbonate and titanium dioxide, and are manufactured usually at a location separate from the end use application, in for example, paper coating and paint manufacturing, and are then stored and held for later transport to the end use location. Because of the high quality standards for the paper and paint final products in which the slurry is used, it is essential that the clay or pigment slurry have a very low microorganism count or content so that it is usable in the paper coating or paint manufacturing.

Yet another important area for controlling microbial growth is cooling systems such as those using cycled up recirculating cooling towers. Such systems maintain a large body of water for a considerable length of time exposed to the atmosphere under conditions which do not include sufficient aeration and exposure to sunlight to provide control of microbial, especially bacterial and fungal, growth. In particular, many cooling towers use fill composed of beads of synthetic polymer or other materials, in order to extend the amount of heat exchange surface area, and this type of construction greatly aggravates the problem of microbiological growth, since it provides an ideal physical environment for the propagation of troublesome microbes. Unchecked, such microorganisms flourish and produce colonies extensive enough to give rise to problems of biofilm blockage of heat exchange surfaces, as well as clogging of the components of the water transporting apparatus used in operating the cooling system. The synergistic combinations of the present invention provide not only excellent control of microbial growth in such systems, but also inhibit the deposition of calcium carbonate scale as well.

The synergistic combination of the present invention has been found especially useful in controlling the harmful effects of microorganisms in water or aqueous media. Systems which utilize circulating water or aqueous media become infected with microorganisms and experience substantial impairment of their efficiency when deposits of the microorganisms build up in the system. The deposits, called slimes, coat the walls of tanks and other vessels, and any machinery or processing equipment which is employed, and create blockages in pipes and valves. The slime formation promotes corrosion of metal surfaces and facilitates the deterioration of wooden towers. The slimes also create discolorations and other imperfections in any products being produced, forcing costly shutdowns. Control of microorganisms in aqueous media is particulary important where there are dispersed particles or fines in the aqueous media, e.g., dispersed cellulosic fibers and dispersed fillers and pigments in papermaking, and dispersed pigments in paint manufacture.

The synergistic antimicrobial combination of the present invention may also be utilized for agricultural and animal health applications, for example in preventing or minimizing the growth of harmful bacteria, yeast, and/or molds on plants, trees, fruit, seeds or soil. The synergistic combination may be useful in treating seed to prevent microorganism, particularly fungal attack. The synergistic combination may also be useful in protecting animal dip compositions against the buildup of microorganisms, and for this purpose may be combined with a veterinary animal dip parasiticide and an acceptable carrier.

2. Brief Description of the Prior Art

Grief, et al., U.S. Pat. Nos. 3,833,731 and 3,877,922; and Hatmetz et al., U.S. Pat. Nos. 3,873,597 describe 2-bromo-2-bromomethyl-glutaronitrile and related compounds and their use as antibacterial, antifungal and algicidal agents.

Hinton et al. U.S. Pat. No. 3,065,123 describes a process for controlling microorganisms in water and aqueous media by the addition of certain 1:2-benzisothiazolones.

British Pat. No. 1,531,431 describes treatment with N-alkyl 1,2-benzisothiazolin-3-ones for controlling microorganisms in water-based paints and adhesives, water-oil emulsions, and metalworking fluids.

Gazzard et al. U.S. Pat. No. 3,970,755 describes biocidal compositions comprising certain quaternary ammonium compounds and 1,2-benzisothiazolin-3-ones.

U.K. Pat. No. 1,458,041 describes a synergistic biocidal composition, especially for aqueous systems, containing isothiazolin-3-ones and 2-thiono-tetrahydro-1,3,5-thiadiazines.

U.S. Pat. No. 4,604,405 discloses synergistic antimicrobial admixtures of 2-bromo-2-bromomethyl-glutaronitrile and 2,2-dibromo-3-nitrilopropionamide.

U.S. Pat. No. 4,612,328 discloses synergistic antimicrobial admixtures of 2-bromomethyl-glutaronitrile and methylene bis(thiocyanate).

U. S. Pat. No. 4,655,815 discloses synergistic antimicrobial admixtures of 2-bromo-2-bromomethyl-glutaronitrile and a formaldehyde donor.

U.S. Pat. No. 4,830,657 discloses synergistic antimicrobial admixtures of 2-bromo-2-bromomethyl-glutaronitrile and 1,2-benzisothiazolin-3-ones.

However, there is no suggestion in any of the above references of the synergistic antimicrobial combination of the present invention.

SUMMARY OF THE INVENTION

The present invention relates to a synergistic antimicrobial admixture comprising an antimicrobially effective amount of:

(A) a polyether polyamino methylene phosphonate of the following formula:

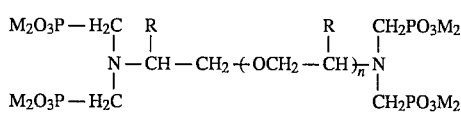

and optionally the N-oxides thereof; where n is an integer or fractional integer which is, or on average is, from about 2 to about 12, inclusive; M is hydrogen or a suitable cation; and each R may be the same or different and is independently selected from hydrogen and methyl; AND (B) one or more members selected from the group consisting essentially of the following non-oxidizing biocides:
didecyl dimethyl ammonium chloride;
dodecylguanidine hydrochloride;
methylene bisthiocyanate;
2,2-dibromo-3-nitrilo-propionamide;
2-(thiocyanomethylthio)benzothiazole/methylene bisthiocyanate;
glutaraldehyde;
potassium dimethyldithiocarbamate;
5-chloro-2-methyl-4-isothiazolin-3-one,
2-methyl-4-isothiazolin-3-one;
tetrahydro-3,5-dimethyl-2,H-1,3,
5-thiadiazin-2-thione;
1,2-dibromo-2,4-dicyanobutane;

A preferred subclass of compositions is that wherein for component (A), in the above formula, M is hydrogen, R is methyl, and n is from about 2 to about 3, most preferably an average of about 2.6.

The present invention also relates to a method of inhibiting microbial growth, comprising contacting the microbial growth with an antimicrobially effective amount of an admixture comprising:

(A) a polyether polyamino methylene phosphonate of the following formula:

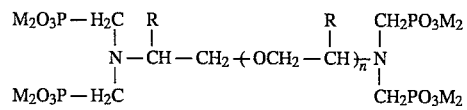

and optionally the N-oxides thereof; where n is an integer or fractional integer which is, or on average is, from about 2 to about 12, inclusive; M is hydrogen or a suitable cation; and each R may be the same or different and is independently selected from hydrogen and methyl; AND (B) one or more members selected from the group consisting essentially of the following non-oxidizing biocides:
didecyl dimethyl ammonium chloride;
dodecylguanidine hydrochloride;
methylene bisthiocyanate;
2,2-dibromo-3-nitrilo-propionamide;
2-(thiocyanomethylthio)benzothiazole.
glutaraldehyde;
potassium dimethyldithiocarbamate;
5-chloro-2-methyl-4-isothiazolin-3-one;
2-methyl-4-isothiazolin-3-one;
tetrahydro-3,5-dimethyl-2,H-1,3,
5-thiadiazin-2-thione;
1,2-dibromo-2,4-dicyanobutane;

The present invention still further relates to a method of inhibiting the formation, deposition and adherence of scale-forming salts in an aqueous system, while at the same time inhibiting microbial growth in said system, comprising the step of adding to said system an amount sufficient to establish a concentration of from 1 to 100 mg/L of an admixture of a polyether polyamino methylenephosphonate of the formula above and a non-oxidizing biocide which is one or more members selected from the group consisting essentially of those recited above.

DETAILED DESCRIPTION OF THE INVENTION

COMPONENT (A)

The first component of the synergistic antimicrobial admixture of the present invention comprises a polyether polyamino methylene phosphonate of the formula:

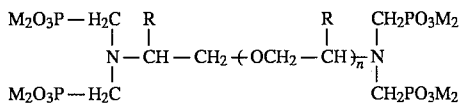

and optionally the N-oxides thereof; where n is an integer or fractional integer which is, or on average is, from about 2 to about 12, inclusive; M is hydrogen or a suitable cation; and each R may be the same or different and is independently selected from hydrogen and methyl.

A preferred subclass of compositions of the above formula is that wherein M is hydrogen, R is methyl, and n is from about 2 to about 3, most preferably an average of about 2.6.

In order to obtain good synergistic antimicrobial results, and also particularly to obtain as well high levels of control of scale deposits, especially under severe conditions of high pH and high calcite concentrations, it has been found that there are certain essential components of the structure of the polyether polyamino methylene phosphonates which are necessary to provide that performance. Thus, e.g., the tetra(aminophosphonate) portion of the structure is essential. Whether these groups are present initially in the phosphonic acid form or as an alkali metal or other salt of the acid, has no real bearing on the performance of the overall molecule. At the pH's under which the compositions of the present invention function, they are, and must be, in their ionized form. Thus, it is not critical whether "M" is hydrogen or a suitable cation, and the selection of an appropriate salt form is well within the skill of the art. In addition to alkali metal salts, ammonium salts: $NH_4^+$, or ammonium derivative salts: $NR_4^+$ (R=alkyl etc ) or mixtures thereof, may be used. Alkali metal salts are the most simple, and are preferred for that reason.

The polyether polyamino methylene phosphonate may be in the N-oxide form: $N \rightarrow O$. This group confers significant resistance to degradation.

Another desirable feature of the polyether phosphonates and N-oxides thereof useful in the synergistic antimicrobial admixtures and methods of the present invention is the isopropyl group which bridges the diphosphonomethylamino group and the polyether group.

The next structural element of the polyether phosphonates and N-oxides to be considered is the polyether moiety:

$$+OCH_2-\underset{\underset{R}{|}}{CH}+_{\overline{n}}$$

R may be hydrogen or methyl, and thus the polyether moiety is either polyoxyethylene or polyoxypropylene, with the polyoxypropylene being preferred. Since the polyether polyamino methylene phosphonates are prepared by phosphonomethylation of the appropriate diamine, the character of the polyether moiety will depend upon the way in which the amine starting material is made. Processes for making such polyether diamines are known in the art; and attention is directed particularly to U.S. Pat. No. 3,236,895, which describes preparation of a variety of polyether diamines especially useful in preparing the phosphonate final products used in the present invention.

In accordance with the processes set out in U.S. Pat. No. 3,236,895 and related processes described in the prior art, it is possible to prepare any one of a number of desired polyether diamines within the scope of the present invention. In the general formula for the polyether polyamino methylene phosphonates used herein, the polyether moiety is simply represented by the formula above. Since R may be hydrogen or methyl, both ethyleneoxy and propyleneoxy units are possible, as already mentioned. Moreover, R is to be independently chosen, i.e., ethyleneoxy and propyleneoxy units may alternate in various patterns, including blocks of each, or they may be all one or the other. For example, the following are just some of the polyether segments which might be prepared to form the basis for the corresponding diamines, which would then be used to make phosphonates within the scope of the present invention (where EO=ethyleneoxy, and PO=propyleneoxy): EO; PO; EO-EO; PO-PO; EO-PO; EO-EO-EO; PO-PO-PO; EO-EO-PO; EO-PO-PO; EO-PO-EO; PO-EO-PO; EO-EO-EO-EO; PO-PO-PO-PO; EO-PO-PO-PO; EO-EO-PO-PO; EO-EO-EO-PO; EO-PO-EO-PO; EO-PO-PO-EO; PO-EO-EO-PO.

In the above examples, "n" in the main formula would be an integer of from 1 to 4. Since "n" is defined as being from 1 to 12, an even larger number of possible polyether moieties is included. However, it has been found that generally the polyether phosphonates of lower molecular weight, i.e., where "n" is a smaller integer, are those which are preferred. Examples of some of these preferred phosphonates are shown in the table below, where Z=methylenephosphonate:

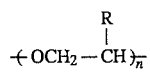

$$Z_2-N-\underset{\underset{R_z}{|}}{CHCH_2}-(OCH_2\underset{\underset{R_a}{|}}{CH})_a-(OCH_2\underset{\underset{R_b}{|}}{CH})_b-NZ_2$$

| Id. No. | a | b | $R_z$ | $R_a$ | $R_b$ |
|---------|---|---|-------|-------|-------|
| A | 2 | 1 | $CH_3$ | H | $CH_3$ |
| B | 2.6* | 0 | $CH_3$ | $CH_3$ | — |
| C | 2 | 0 | $CH_3$ | $CH_3$ | — |
| D | 8.5* | 1 | $CH_3$ | H | $CH_3$ |
| E | 5.6* | 0 | $CH_3$ | $CH_3$ | — |
| F | 2 | 0 | H | H | — |
| G | 3 | 0 | H | H | — |
| H | 3 | 0 | $CH_3$ | $CH_3$ | — |
| I | 3 | 1 | H | $CH_3$ | H |
| J | 4 | 0 | H | $CH_3$ | — |

* = the value of "n" on average.

It will be noted from the table above that in several cases, "n" has an average value, i.e., the number of repeating ethyleneoxy or propyleneoxy units may vary. Thus, it is possible to have a mixture of varying chain lengths of polyoxyethylene or polyoxypropylene in the final product. This is also contemplated to be within the scope of the present invention, so long as the requirements with respect to the limit of "n" are observed. Consequently, while "n" is merely defined as an integer or fractional integer which is, or on average is, from about 2 to about 12, it has two aspects. It defines the total of the number of repeating ethyleneoxy and/or propyleneoxy units considered separately, and thus if "n" is, e.g., 4, it includes 4 propyleneoxy units, 3 propyleneoxy units and 1 ethyleneoxy unit, 2 propyleneoxy units and 2 ethyleneoxy units, and so forth.. The value of "n" may also represent an average number, and this is always the case, of course, when it is a fractional integer. In this case, for each of the ethyleneoxy and/or propyleneoxy units considered separately, mixtures of these units may be present so as to give an average value for "n". For example, in the table above, for Id. No. D, the total of "a" and "b" is 9.5, which is the value of "n". What is described is a mixture of polyether phosphonates in which all of them have an isopropyl bridging group and an ethyleneoxy moiety, but the repeating propyleneoxy units are such that on average their value is about 8.5.

The number of repeating ethyleneoxy or oxypropylene units, designated by the subscript "n", determines the total molecular weight of the overall polyether phosphonate. It has been found that in order to achieve optimum synergistic antimicrobial results, as well as, particularly, provide adequate scale control under the severe conditions of use defined herein, it is necessary that "n" be an integer or fractional integer which is, or on average is, from about 2 to about 12, inclusive.

As discussed above, the reason for "n" being potentially a fractional integer arises from the fact that the primary diamine from which the polyether polyamino methylene phosphonates are prepared by phosphonomethylation may be a mixture of polyethers in which "n" is two or more of 2, 3, 4, 5 and so forth, in varying proportions. For example, a preferred polyether polyamino methylene phosphonate for use in the compositions and methods of the present invention has a molecular weight of approximately 632 and the value of "n" on average is about 2.6. Thus, this type of polyether phosphonate has a molecular weight distribution, i.e., of the various polyoxypropylenes which make it up, and this distribution is represented by a fractional integer average value for "n". But, it is also within the scope of the present invention for "n" to be a whole integer, e.g., "3", which usually designates a single molecular weight and not a molecular weight distribution.

The polyether phosphonates and corresponding N-oxides of the synergistic antimicrobial admixtures and methods of the present invention are prepared first by phosphonomethylation of the appropriate primary diamine which already contains the polyoxyethylene and polyoxypropylene moieties, followed by an oxidation step which provides the N-oxide moieties..

Such primary amine starting materials such as Jeffamine D230 and their method of preparation are well known. The phosphonomethylation of the primary diamine is then carried out by a Mannich reaction such as that described in K. Moedritzer and R. Irani, *J. Organic Chem.* 31(5) 1603–7, "The Direct Synthesis of alpha-Aminomethyl Phosphonic Acids; Mannich-Type Reactions with Orthophosphorous Acid", May 1966. In a typical reaction, the primary diamine is added to a mixture of phosphorous acid and water, and concentrated hydrochloric acid is then added slowly, after which the reaction mixture is heated to reflux with addition of aqueous formaldehyde.

Although the general structural formula employed herein indicates that the nitrogen atom is completely phosphonomethylated, as a practical matter, preparation of the polyether polyamino methylene phosphonates of the present invention, as described in detail further below, usually results in only about 80 to 90% phosphonomethylation. Other side products give N-substitution with H, $CH_3$, $CH_2OH$, etc. It is not practical, as a matter of simple production economics, however, to isolate and purify the completely phosphonomethylated compounds, since the side products just described do not interfere with scale deposit inhibition. Such side products, are consequently, usually allowed to remain, and the test data set out further below is based on test samples containing such side products. Consequently, the activity levels obtained would be even higher were 100% active compound being tested.

Once the desired phosphonomethylated polyoxypropylene diamine has been prepared as described above, the N-oxide final product of the present invention is then prepared by a step of oxidation, which may be accomplished, e.g., simply by adding hydrogen peroxide to a basic solution of the phosphonomethylated diamine and heating the reaction mixture, which gives high yields of the N-oxide final product. Of course, it is also possible to use other well known techniques for carrying out such a step of oxidation, and any number of these may be successfully employed.

When any of the polyether polyamino methylene phosphonate components of the synergistic antimicrobial admixtures of the present invention are used to inhibit microbial growth, especially in an aqueous system, they can be effectively employed for that purpose when added in amounts sufficient to establish a concentration in said aqueous system of from 1 to 100 mg/L. Preferably, the amount added will be sufficient to establish a concentration of from 5 to 75 mg/L, and most preferably, the amount added will be sufficient to establish a concentration of from 10 to 50 mg/L of the composition. For example, a typical dosage amount would be 25 mg/L. It is understood, however, that many factors, of the type which have been explained in detail with regard to the background to the present invention, will determine the actual amount of the polyether phosphonate components of the present invention which will be added in order to achieve the maximum amount of inhibition of microbial growth in that system. The calculation of those amounts is well within the skill of the artisan in this field.

COMPONENT (B)

The second component of the synergistic antimicrobial admixtures of the present invention is one or more members selected from the group consisting essentially of the following non-oxidizing biocides:

didecyl dimethyl ammonium chloride;

dodecylguanidine hydrochloride;

methylene bisthiocyanate;

2,2-dibromo-3-nitrilo-propionamide;

2-(thiocyanomethylthio)benzothiazole.

glutaraldehyde;

potassium dimethyldithiocarbamate;

5-chloro-2-methyl-4-isothiazolin-3-one;

2-methyl-4-isothiazolin-3-one;

tetrahydro-3,5-dimethyl-2,H-1, 3, 5-thiadiazin-2-thione;

1,2-dibromo-2,4-dicyanobutane;

All of these non-oxidizing biocides are commercially available and used extensively in various industrial applications. They are diverse in chemical structure and only have in common the fact that they act synergistically with the polyether phosphonate components (A) when used in admixture to inhibit microbial growth.

When any of the non-oxidizing biocides components of the synergistic antimicrobial admixtures of the present invention are used to inhibit microbial growth, especially in an aqueous system, they can be effectively employed for that purpose when added in amounts sufficient to establish a concentration in said aqueous system of from 0.5 to 50 mg/L. Preferably, the amount added will be sufficient to establish a concentration of from 1.0 to 25 mg/L, and most preferably, the amount added will be sufficient to establish a concentration of from 3.0 to 20 mg/L of the composition. However, it will be appreciated that the dosage of the individual non-oxidizing biocide will vary from biocide to biocide because of their diversity, and the most accurate guide to the correct dosage is the dosage at which each individual non-oxidizing biocide is conventionally applied to achieve inhibition of microbial growth in various applications areas. It will be understood, then, that many factors, of the type which have been explained in detail with regard to the background to the present invention, will determine the actual amount of the non-oxidizing biocides components of the present invention which will be added in order to achieve the maximum amount of inhibition of microbial growth in that system. The calculation of those amounts is well within the skill of the artisan in this field.

The proportions of the two components of the synergistic combination are dictated by the dosage levels of each component, based on 100% active ingredient, which will be employed in each end use application. The recommended dosage levels are described in detail below.

The synergistic antimicrobial admixture active ingredient components of the antimicrobial compositions of the present invention may be used in diverse formulations: solid, including finely divided powders and granular materials; as well as liquid, such as solutions, emulsions, suspensions, concentrates, emulsifiable concentrates, slurries and the like, depending upon the application intended, and the formulation media desired. Further, when the synergistic antimicrobial combination is liquid, it may be employed neat or may be incorporated into various formulations, both solid and liquid, as an adsorbate on suitable inert carriers such as talc, clays, diatomaceous earth and the like.

Thus, it will be appreciated that the synergistic antimicrobial admixtures may be employed to form antimicrobial formulations containing the combination as the essential active ingredient, which formulations may also contain a variety of carrier materials adaptable to industrial and agricultural applications including finely divided dry or liquid diluents, extenders, clays, diatomaceous earth, talc and the like, or water and various organic liquids such as lower alkanols, kerosene, benzene, toluene and other petroleum distillate fractions or mixtures thereof.

It will be understood also that the synergistic antimicrobial admixture active ingredients may be used in combination with other antimicrobial materials. For example, the combination can be further combined with other fungicides and bactericides such as 2-(4'-thiazolyl)benzimidazole, sorbic acid, propionic acid, mycostatin, sodium diacetate, trichomycin amphotericin, griseofulvin, undecylenic acid, esters of parahydroxybenzoic acid, chlorguinaldol, 5,7-dichloro-8-hydroxyquinoline, sodium-o-phenylphenate, o-phenylphenol, biphenyl chlorinated phenols, sodium benzoate in appropriate concentrations and in appropriate instances so as to combine the action of each to obtain particularly useful results. Such combinations might find particular application in the preparation of germicidal soaps, in the production of cosmetics and aqueous coatings and in combatting paper mill slime accumulations. It is quite clear also that the synergistic antimicrobial admixtures can be combined with other algicidal agents such as benzalkonium chlorides and other quaternary ammonium compounds to obtain formulations particularly suitable to special problems of algae control.

Thus, in accordance with the present invention there is provided a method of killing or inhibiting the growth or propagation of at least one of: bacteria, yeast, mold, and algae, in dormant, immature, developing and/or mature stages, comprising contacting said bacteria, yeast, mold, or algae, with a bactericidally, fungicidally, or algicidally effective amount of the synergistic antimicrobial admixtures comprising a polyether phosphonate and one or more specifically recited non-oxidizing biocides.

As noted above, the instant invention is based upon the discovery that the synergistic antimicrobial admixtures described above are effective in controlling the growth of bacteria, yeast, fungi and algae in industrial and possibly agricultural applications. It is likely, for example, that the combination is an effective antimicrobial for the destruction or control of soil fungi and bacteria and for the protection of seeds, bulbs, and plants. Also, it may be useful as an effective algicide in the treatment of pools and ponds, cooling water systems and the like. The synergistic antimicrobial combination of this invention may be useful not only against bacteria and fungi responsible for stunting growth, and even destruction of many types of crop-producing plants, but also against those causing degradation and deterioration of many types of industrial products including, for example, paper, leather, wood preservation, textiles, aqueous systems such as adhesives, resins, drilling fluids, pigment dispersions and latex paints and oleoresinous coatings whose films are particularly vulnerable to the destructive action of fungi. The formation of slime by microorganisms in the water from cooling towers can be minimized with the present invention, thus avoiding the deterioration, corrosion, fouling and decreased efficiency of the cooling system which would otherwise result. The large economic losses encountered in pulping and papermaking operations caused by the accumulation of bacterial and fungal slimes in various parts of the system can be eliminated to a significant extent by use of the synergistic admixtures described herein.

The antimicrobial methods of treatment of the present invention involve contacting the microorganisms involved with the synergistic antimicrobial admixtures. This can be accomplished either by simple addition of the two or more components of the combination together as a single composition, or by addition of the two or more components separately. Such separate co-administration can either be at the same time or at different times. The net effect will be the same: the article or system being treated will ultimately have incorporated therein or have applied thereto the desired dosage concentration of each component.

In the treatment of aqueous systems, such as cooling water systems, paper and pulp mill systems, pools, ponds, lagoons, lakes, etc., to control the growth and/or propagation formation of microorganisms the two components of the combination may be added together as a single composition at one or at multiple points in the system, or may be added separately, at the same or at different points and/or times of introduction, thus resulting in the desired antimicrobial effect.

The antimicrobial activity of the synergistic antimicrobial admixtures and individual components thereof described above has been confirmed using standard laboratory techniques. They have been found to be effective, for example, in inhibiting bacteria including *Klebsiella pneumoniae pneumonias, Pseudomonas aeruginosa*, and Micrococcus sp. They should also be effective against other bacteria and fungi including Penicillium species, Saccharomyces species, including *S. cerevisiae*, Candida species, Fusarium species, Aspergillus species, and Cephalosporium species. Such bacteria and/or fungi commonly are found on cereal and grain products, in clay and pigment slurries, in oils, on fruits and vegetables and on cosmetics, leather, electrical insulation, textiles and numerous other materials capable of supporting their growth. Also, such bacteria and/or fungi may be found on plants, seeds, fur and wood and in soils. Further, they may be used to control overgrowth of algae such as Chlorella sp. including *C. pyrenoidosa*.

As noted above, it is expected that growth of various harmful fungi and bacteria existing in soil can be eliminated or limited by use of formulations containing the synergistic antimicrobial admixtures described herein. The term "soil" as used here is intended to include all media capable of supporting growth of plants and may include humus, sand, manure, compost, artificially created plant growth solutions and the like.

The synergistic antimicrobial admixtures described above have activity against bacteria, yeast, mold, and/or algae when employed at appropriate levels of concentration and may be used to inhibit growth of these organisms. It will be obvious to those skilled in the art that the required effective concentration will vary with particular organisms and in particular applications. In general, however, effective fungicidal, bactericidal and algicidal response is obtained then when the synergistic antimicrobial admixture is employed in concentrations ranging between 1 and 200 ppm (parts per million), preferably 1 and 50 ppm, of polyether phosphonate; and between 1 and 1000 ppm, preferably 1 to 880 ppm, of non-oxidizing biocide, and in a weight ratio of polyether phosphonate/non-oxidizing biocide (on an active basis) of 10:1 to 1:5, preferably 5:1 to 1:3, and even more preferably 3:1 to 1:2. Such levels may be achieved by the administration of the two components of the admixture together as a single composition (optionally comprising other antimicrobial materials and/or inert carriers and excipients), or separately at the same or different points and/or times of introduction.

For other applications of the type described above, amounts of from 0.005 to 1.0% by weight, based on weight of the substrate being treated, of the synergistic antimicrobial combination of the present invention is incorporated into, sprayed onto, used to dip, or otherwise applied to the substrate to be treated in order to prevent growth of bacteria, fungi (including yeasts and molds) and algae.

Of course, the precise dosages of the components which will be employed depends upon a number of factors. First, the dosage is indicated in parts per million (ppm), which refers to the concentration of the active ingredient in the environment being treated, for example, the concentration of DGH in a cooling water system. This concentration is based on 100% active ingredient for convenience in evaluating and comparing test data. In actual practice, however, various percentages of active ingredient may actually be used, with the balance of the composition being added comprising conventional excipients such as dispersants, stabilizers, preservatives, co-solvents, diluents, and the like.

The components of the synergistic antimicrobial admixtures of the present invention may be added to an article or system to be treated as separate entities, or as combination. The two components may be combined simply as active ingredients, or may additionally be combined with commonly employed carriers and excipients, as described above.

Although it is believed that the synergistic activity exhibited by the two components is due to their presence as discrete chemical entities, chemical reaction between the two and the formation of adducts or cross-reaction products is possible. Such additional active species are also encompassed within the scope of the instant invention.

The following examples will serve to further illustrate the present invention but should not be construed in any way as being a limitation on the scope thereof.

EXAMPLES OF PREFERRED EMBODIMENTS

Two series of experiments were set up which consisted of 50 ml solutions of deionized water adjusted to pH 9 with sodium hydroxide. All the experimental solutions were inoculated with a mixed environmental bacteria, capped and held at ambient room temperature. The first series consisted of a control, containing no biocide, and other solutions each containing a non-oxidizing registered biocide at a typical use concentration. The second series consisted of a second control containing only the tetra methylene phosphonate of Jeffamine*D-230 (Papemp), and other solutions each containing a non-oxidizing registered biocide at a typical use concentration plus 25 mg/L active Papemp. At three hours of contact time, a one milliliter aliquot was removed from each solution and bacteria levels were measured using the standard plate count procedure. This bacterial measurement was repeated again at 24 hours of contact time.

EXAMPLE 1

| | Percent Bacterial Kill | |
|---|---|---|
| | 20 mg/L Didecyl Dimethyl Ammonium Chloride | 20 mg/L Didecyl Dimethyl Ammonium Chloride and 25 mg/L PAPEMP |
| 3 Hours Kill | 90% | 99% |
| 24 Hours Kill | 83% | 89% |

EXAMPLE 2

| | Percent Bacterial Kill | |
|---|---|---|
| | 12.8 mg/L Dodecylguanidine Hydrochloride | 12.8 mg/L Dodecylguanidine Hydrochloride and 25 mg/L PAPEMP |
| 3 Hours Kill | 90% | 99% |
| 24 Hours Kill | 67% | 89% |

EXAMPLE 3

| | Percent Bacterial Kill | |
|---|---|---|
| | 7.5 mg/L Methylene Bisthiocyanate | 7.5 mg/L Methylene Bisthiocyanate and 25 mg/L PAPEMP |
| 3 Hours Kill | 70% | 93% |
| 24 Hours Kill | 17% | 89% |

EXAMPLE 4

| | Percent Bacterial Kill | |
|---|---|---|
| | 3.75 mg/L 2,2-Dibromo-3-Nitrilo-Propionamide | 3.75 mg/L 2,2-Dibromo-3-Nitrilo-Propionamide and 25 mg/L PAPEMP |

EXAMPLE 5

| | Percent Bacterial Kill | |
|---|---|---|
| | 15 mg/L 2-(Thiocyano Methylthio) Benzothiazole/ Methylene Bisthiocyanate | 15 mg/L 2-(Thiocyano Methylthio) Benzothiazole/ Methylene Bisthiocyanate and 25 mg/L PAPEMP |
| 3 Hours Kill | 66% | 99% |
| 24 Hours Kill | 0% | 83% |

EXAMPLE 6

| | Control Bacterial Levels | |
|---|---|---|
| | Control #1 No Additives | Control #2 25 mg/L PAPEMP |
| 3 Hours Count | 250,000 | 3,500,000 |
| 24 Hours Count | 30,000 | 175,000 |

Following the procedures described above, but at pH 7.0, the results set out below were obtained.

EXAMPLE 7

| | Percent Bacterial Kill | |
|---|---|---|
| | 27 mg/L glutaraldehyde | 27 mg/L glutaraldehyde and 25 mg/L PAPEMP |
| 3 Hours Kill | 0% | 62% |

| | 25 mg/L Potassium Di- methyl dithiocarbamate | 25 mg/L Potassium Di- methyl dithiocarbamate and 25 mg/L PAPEMP |
|---|---|---|
| 3 Hours Kill | 0% | 37% |

| | 35 mg/L 5-chloro-2- 4-isothiazolin-3-one and 2-methyl-4-iso thiazolin-3-one | 35 mg/L 5-chloro-2- 4-isothiazolin-3-one and 2-methyl-4-iso- thiazolin-3-one and 25 mg/L PAPEMP |
|---|---|---|
| 3 Hours Kill | 0% | 39% |

| | 59 mg/L 1,2-dibromo- 2,4-dicyanobutane | 59 mg/L 1,2-dibromo 2,4-dicyanobutane and 25 mg/L PAPEMP |
|---|---|---|
| 3 Hours Kill | 0% | 39%—. |

3 Hours Kill 90% 99%
24 Hours Kill 0% 89%

What is claimed is:

1. A synergistic antimicrobial admixture useful for inhibiting microbial growth in an aqueous system comprising an antimicrobially effective amount sufficient to establish a concentration of from 1 to 100 mg/L of an admixture of:

(A) a polyether polyamino methylene phosphonate of the following formula:

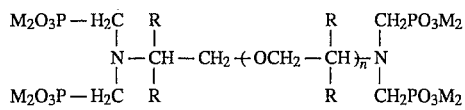

and optionally the N-oxides thereof; where n is an integer or fractional integer which is, or on average is, from about 2 to about 12, inclusive; M is hydrogen or a suitable cation; and each R may be the same or different and is independently selected from hydrogen and methyl; AND (B) one or more members selected from the group consisting of the following non-oxidizing biocides:
didecyl dimethyl ammonium chloride;
dodecylguanidine hydrochloride;
methylene bisthiocyanate;
2,2-dibromo-3-nitrilo-propionamide; and
2-(thiocyanomethylthio)benzothiazole/methylene bisthiocyanate.

2. An admixture according to claim 1 wherein for component (A), in the above formula, M is hydrogen, R is methyl, and n is on average about 2.6.

3. A method of inhibiting microbial growth in an aqueous system, comprising the step of adding to said system an antimicrobially effective amount sufficient to establish a concentration of from 1 to 100 m/L of an admixture comprising:

(A) a polyether polyamino methylene phosphonate of the following formula:

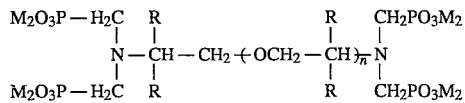

and optionally the N-oxides thereof; where n is an integer or fractional integer which is, or on average is, from about 2 to about 12, inclusive; M is hydrogen or a suitable cation; and each R may be the same or different and is independently selected from hydrogen and methyl; AND (B) one or more members selected from the group consisting of the following non-oxidizing biocides:
didecyl dimethyl ammonium chloride;
dodecylguanidine hydrochloride;
methylene bisthiocyanate;
2,2 -dibromo-3-nitrilo-propionamide;
2-(thiocyanomethylthio)benzothiazole/methylene bisthiocyanate; and
1,2-dibromo-2,4-dicyanobutane.

4. A method according to claim 3 wherein for component (A), in the above formula, M is hydrogen, R is methyl, and n is on average about 2.6.

5. A synergistic antimicrobial admixture useful for inhibiting microbial growth in an aqueous system comprising an antimicrobially effective amount sufficient to establish a concentration of from 1 to 100 mg/L of an admixture of:

(A) a polyether polyamino methylene phosphonate of the following formula:

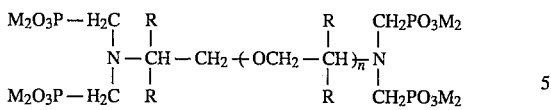

and optionally the N-oxides thereof; where n is an integer or fractional integer which is, or on average is, from about 2 to about 12, inclusive; M is hydrogen or a suitable cation; and each R may be the same or different and is independently selected from hydrogen and methyl; AND (B) one or more members selected from the group consisting of the following non-oxidizing biocides:

didecyl dimethyl ammonium chloride;
dodecylguanidine hydrochloride;
methylene bisthiocyanate;
2,2-dibromo-3-nitrilo-propionamide;
2-(thiocyanomethylthio)benzothiazole/methylene bisthiocyanate;
glutaraldehyde;
potassium dimethyldithiocarbamate;
5-chloro-2-methyl-4-isothiazolin-3-one,2-methyl-4-isothiazolin-3one; and
1,2-dibromo-2,4-dicyanobutane.

* * * * *